United States Patent [19]

Amplatz et al.

[11] Patent Number: 5,098,393
[45] Date of Patent: Mar. 24, 1992

[54] MEDICAL INTRODUCER AND VALVE ASSEMBLY

[76] Inventors: Kurt Amplatz, Ten Evergreen Rd., St. Paul, Minn. 55110; Frank Kotula, 153457 70th Pl., Maple Grove, Minn. 55369

[21] Appl. No.: 200,662

[22] Filed: May 31, 1988

[51] Int. Cl.⁵ .............................................. A61M 5/18
[52] U.S. Cl. .................................. 604/167; 604/164; 604/166; 604/172
[58] Field of Search ............................. 604/158–167, 604/169–172, 256, 264, 265, 274, 280, 283, 174, 177, 179; 128/877, DIG. 6, DIG. 26; 137/845, 246; 251/149.1, 149.3

[56] References Cited

U.S. PATENT DOCUMENTS

| | | | |
|---|---|---|---|
| 1,089,805 | 10/1914 | Wolf. | |
| 2,328,327 | 8/1943 | Cobb | 251/149.3 |
| 2,687,707 | 8/1954 | O'Shei | 121/142 |
| 3,030,953 | 4/1962 | Koehn | 128/214 |
| 3,067,425 | 12/1962 | Colley | 2/6 |
| 3,082,769 | 3/1963 | Palmer | 128/221 |
| 3,388,703 | 6/1968 | Bowes | 128/214.4 |
| 3,406,685 | 10/1968 | May | 128/214.4 |
| 3,416,567 | 12/1968 | Von Dardel et al. | 137/604 |
| 3,492,992 | 2/1970 | Kurtz | 128/214.4 |
| 3,556,294 | 1/1971 | Walck | 604/172 |
| 3,612,050 | 10/1971 | Sheridan | 128/214.4 |

(List continued on next page.)

FOREIGN PATENT DOCUMENTS

| | | | |
|---|---|---|---|
| 0023580 | 2/1981 | European Pat. Off. | 604/177 |
| 0150281 | 8/1985 | European Pat. Off. . | |
| 1809364 | 3/1968 | Fed. Rep. of Germany . | |
| 2015524 | 4/1969 | Fed. Rep. of Germany . | |
| 8301575 | 5/1983 | PCT Int'l Appl. . | |

OTHER PUBLICATIONS

Butto et al., "The Modified Sheath Introducer for Reduced Arterial Damage", *Radiology* 163: 824–826, Jun. 1987.

*Primary Examiner*—John D. Yasko
*Assistant Examiner*—A. Gutowski
*Attorney, Agent, or Firm*—Fish & Richardson

[57] ABSTRACT

A medical catheter introducer and hemostasis valve assembly consists of a sheath having an elongated tube defining a conduit, a housing disposed at the proximal end of the sheath and further defining a conduit and an orifice, and a flexible elongated dilator sized for insertion through the hub and sheath conduit. The dilator has a tapered distal tip end and defines an axial conduit and an annular ridge having distally- and proximally-directed inclined surfaces. The sheath, when assembled with the dilator, has its distal end immediately adjacent the proximally-directed inclined surface of the ridge. A hemostasis valve for sealing the conduit is disposed in alignment with the conduit, and defines an aperture for passage of dilator and ridge therethrough in sealing engagement, into the conduit, and seals when the dilator is removed. The valve has a housing defining an orifice of a first diameter, and a valve element of a second diameter, greater than the first diameter. The valve is disposed within the orifice and is subject to externally-applied, radially directed forces that cause the valve to assume a dome-shape formation, with a convex surface disposed against the pressure of fluids within the body. As the introducer assembly is introduced into a body over a guidewire extending via a puncture opening into a vessel, the dilator and sheath flex to follow the guidewire, and the tapered end of the dilator and the distally-directed inclined surface of the ridge act to dilate the flesh about the opening to facilitate passage of the sheath. The introducer and valve may be used alone, or respectively with valves or introducers of other design. A base for attachment of the introducer to the patient is also described.

13 Claims, 4 Drawing Sheets

U.S. PATENT DOCUMENTS

| | | | |
|---|---|---|---|
| 4,315,513 | 2/1982 | Nawash et al. | 128/348 |
| 4,318,401 | 3/1982 | Zimmerman | 128/214 R |
| 3,739,778 | 6/1973 | Monestere, Jr. et al. | 128/214.4 |
| 3,788,327 | 1/1974 | Donowitz et al. | 128/350 R |
| 3,827,434 | 8/1974 | Thompson | 128/214.4 |
| 3,853,127 | 12/1974 | Spademan | 128/214.4 |
| 3,895,632 | 7/1975 | Plowiecki | 128/214.4 |
| 3,915,168 | 10/1975 | Monestere, Jr. et al. | 128/214.4 |
| 4,000,739 | 1/1977 | Stevens | 128/214.4 |
| 4,096,860 | 6/1978 | McLaughlin | 128/214.4 |
| 4,143,853 | 3/1979 | Abramson | 251/149.1 |
| 4,166,469 | 9/1979 | Littleford | 128/784 |
| 4,177,814 | 12/1979 | Knepshield et al. | 128/348 |
| 4,239,042 | 12/1980 | Asai | 128/214.4 |
| 4,240,411 | 12/1980 | Hosono | 128/4 |
| 4,250,881 | 2/1981 | Smith | 128/214.4 |
| 4,334,551 | 6/1982 | Pfister | 137/614.03 |
| 4,335,718 | 6/1982 | Calabrese | 128/218 N |
| 4,354,491 | 10/1982 | Marbry | 128/214.4 |
| 4,364,392 | 12/1982 | Strother et al. | 128/325 |
| 4,387,879 | 6/1983 | Tauschinski | 251/149.1 |
| 4,411,655 | 10/1983 | Schreck | 604/165 |
| 4,412,836 | 11/1983 | Brignola | 604/87 |
| 4,422,447 | 12/1983 | Schiff | 128/1 |
| 4,424,833 | 1/1984 | Spector et al. | 137/849 |
| 4,425,122 | 1/1984 | Cohen | 604/237 |
| 4,430,081 | 2/1984 | Timmermans | 604/256 |
| 4,434,810 | 3/1984 | Atkinson | 137/493 |
| 4,436,519 | 3/1984 | O'Neill | 604/175 |
| 4,443,219 | 4/1984 | Meisch et al. | 604/317 |
| 4,449,693 | 5/1984 | Gereg | 251/149.8 |
| 4,451,252 | 5/1984 | Martin | 604/43 |
| 4,451,256 | 5/1984 | Weikl et al. | 604/164 |
| 4,464,171 | 8/1984 | Garwin | 604/53 |
| 4,464,175 | 8/1984 | Altman et al. | 604/99 |
| 4,473,067 | 9/1984 | Schiff | 128/1 |
| 4,475,548 | 10/1984 | Muto | 128/207 |
| 4,496,348 | 1/1985 | Genese et al. | 604/167 |
| 4,509,944 | 4/1985 | King | 604/53 |
| 4,510,933 | 4/1985 | Wendt et al. | 128/207.14 |
| 4,511,359 | 4/1985 | Vaillancourt | 604/411 |
| 4,535,818 | 8/1985 | Duncan | 137/846 |
| 4,566,493 | 1/1986 | Edwards et al. | 137/846 |
| 4,585,444 | 4/1986 | Harris | 604/177 |
| 4,597,758 | 7/1986 | Aalto et al. | 604/256 |
| 4,610,469 | 9/1986 | Wolff-Mooij | 285/260 |
| 4,610,665 | 9/1986 | Mastsumoto et al. | 604/167 |
| 4,610,671 | 9/1986 | Luther | 604/168 |
| 4,626,245 | 12/1986 | Weinstein | 604/167 |
| 4,634,424 | 1/1987 | O'Boyle | 604/51 |
| 4,634,432 | 1/1987 | Kocak | 604/167 |
| 4,634,433 | 1/1987 | Osborne | 604/171 |
| 4,653,477 | 3/1987 | Akui et al. | 128/4 |
| 4,653,539 | 3/1987 | Bell | 137/860 |
| 4,655,752 | 4/1987 | Honkanen et al. | 604/256 |
| 4,668,221 | 5/1987 | Luther | 604/164 |
| 4,673,393 | 6/1987 | Suzuki | 604/167 |
| 4,683,916 | 8/1987 | Raines | 137/854 |
| 4,705,511 | 11/1987 | Kocak | 604/282 |
| 4,715,360 | 12/1987 | Akui et al. | 128/4 |
| 4,747,833 | 5/1988 | Kousai et al. | 604/164 |
| 4,809,679 | 3/1989 | Shomonaka | 604/167 |
| 4,909,798 | 4/1990 | Fleischhacker et al. | 604/167 |
| 4,960,412 | 10/1990 | Fink | 604/167 |

MEDICAL INTRODUCER AND VALVE ASSEMBLY

The invention relates to medical devices for introducing catheters or the like into blood vessels of the body.

Catheter introducers provide a reusable conduit for passage of catheters and other medical devices, e.g., guidewires, through the body flesh into a blood vessel or other body passageway. Often, the introducer includes or is used with a hemostasis valve for reducing loss of blood by restricting flow about the catheter when in place through the introducer and after it is removed.

Smith U.S. Pat. No. 4,250,881 describes a rigid device for insertion of a catheter, consisting of a needle over which the catheter is placed, the needle having a sweged portion or bulb near its distal end to reduce bunching or folding of the catheter in accordion-like fashion as the needle-and-catheter assembly is inserted into the flesh. Hemostasis valves for use with such introducers, or in other applications, including with dome-shapes for sealing action, have been described by Abramson U.S. Pat. No. 4,143,853; McLaughlin U.S. Pat. No. 4,096,860 and O'Neill U.S. Pat. No. 4,436,519.

SUMMARY OF THE INVENTION

According to the invention, a medical catheter introducer and hemostasis valve assembly comprises an introducer sheath comprising an elongated tubular element defining an introducer conduit, an introducer housing disposed at the proximal end of said introducer sheath and further defining a conduit therethrough and an orifice, a flexible elongated dilator sized and constructed for insertion through the conduit of the introducer hub and introducer sheath, the dilator having a tapered distal tip end portion and defining an axial conduit therethrough, the dilator further defining an annular ridge having distally- and proximally-directed inclined surfaces, the introducer sheath, when assembled with the dilator, having its distal end immediately adjacent the proximally-directed inclined surface of the dilator ridge, and a hemostasis valve adapted for sealing the conduit and disposed in alignment with it, the valve defining an aperture for passage of dilator and ridge therethrough in sealing engagement, into the conduit, and adapted to seal when the dilator is removed, the hemostasis valve comprising a housing defining an orifice of a first diameter, and a valve element of a second diameter relatively greater than the first, the valve disposed within the orifice being subjected to externally-applied, radially directed forces to cause the valve element to assume a dome-shape formation, with a convex surface disposed against pressure of fluids within the body, whereby, as the assembly is introduced into a body over a guidewire extending via a puncture opening into a body vessel, the dilator and sheath are adapted to flex to follow the guidewire, and the tapered end of the dilator and the distally-directed inclined surface of the dilator ridge act to dilate the flesh about the opening to facilitate passage of the sheath therethrough.

The introducer assembly and the hemostasis valve described above in combination may be used separately alone, or may be used, respectively, with valves or introducers of other design.

Preferred embodiments may include one or more of the following features. The ridge is immediately distal of the tapered portion of the dilator. The dilator further comprises a proximal hub, and the introducer housing and dilator hub define cooperating means for fixedly positioning the distal end of the introducer sheath immediately adjacent the proximally-directed inclined surface of the dilator ridge. The introducer assembly of the invention used alone may further comprise a hemostasis valve disposed relative to the conduit, and defining an aperture for passage of dilator and ridge therethrough in sealing engagement, into the conduit. Preferably the introducer housing defines an orifice, and the hemostasis valve is disposed therewithin, the valve comprising a housing defining an orifice of a first diameter, and a valve element of a second diameter relatively greater than the first diameter, the valve element disposed within the orifice being subjected to externally-applied, radially directed forces to cause the valve element to assume a dome-shape formation, with a convex surface disposed against the pressure of fluids within the body. The introducer housing defines a second conduit for passage of fluid into the conduit defined by the introduced sheath, preferably the second conduit is distal of an associated hemostasis valve. The introducer assembly further comprises a base element for affixing the introducer assembly to the skin surface of a patient, comprising a center portion having a front edge and a pair of side edges, a pair of wing portions hinged to the center portion at the side edges, and an upper base portion hinged to the center portion at the front edge, the upper base portion defining means for receiving the introducer housing and holding it against accidental rotation of the housing, the upper base portion adapted to be disposed at an upraised angle to said center portion. The second diameter is about 10% greater than the first diameter. The hemostasis valve assembly further comprises a valve cup element defining an orifice and, disposed therewithin, lubricating means for lubricating a catheter or the like for encounter with the aperture of the valve element, and a seal means for retaining lubricant within the housing, preferably the lubricating means comprises a silicone soaked sponge. The housing and valve cup define cooperating means for engaging opposite surfaces of the valve element for holding it in position within the housing.

According to another aspect of the invention the base element described above may be employed to secure introducer assemblies of other design.

These and other features and advantages of the invention will be seen from the following description of the presently preferred embodiment, and from the claims.

DESCRIPTION OF THE PREFERRED EMBODIMENTS

The drawings will first briefly be described.

DRAWINGS

FIGS. 7-10 are various views of the connection of a introducer body to a base; specifically.

STRUCTURE

Figure 1:
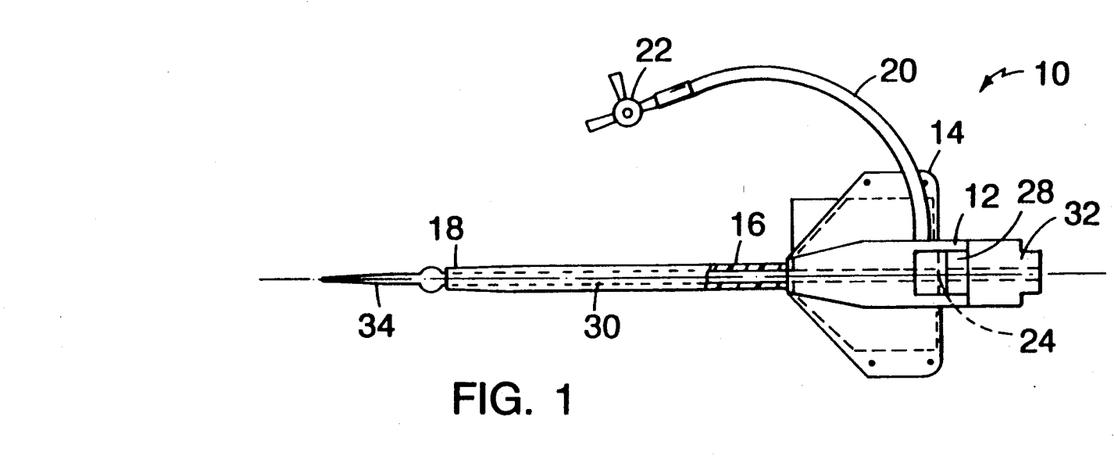
FIG. 1 is a diagrammatic representation of a catheter introducer.

Referring to FIG. 1, catheter introducer 10 consists of an introducer body 12, disposed on a base 14, having an elongated catheter sheath 16, formed, e.g., of Teflon TM, with a tapered distal end portion 18. Connected to introducer body 12 is an elongated tube 20 having a stopcock 22 at its proximal end. Tube 20 is connected to introducer body 12 downstream of a hemostasis valve assembly 24, indicated generally by dashed line.

The valve assembly is held in place by housing cap 28. The introducer 10 may be used with an elongated dilator 30 having a proximal hub 32. Dilator 30 has a tapered distal end 34 and a circular ridge 36 near the end of the taper. The dilator longitudinally defines a central channel 31 running the length of dilator to a distal aperture 33 of internal diameter (0.035 inch) approximately equal to the outer diameter of a guidewire used to introduce dilator 30 into a body cavity, as described below.

Figure 2:
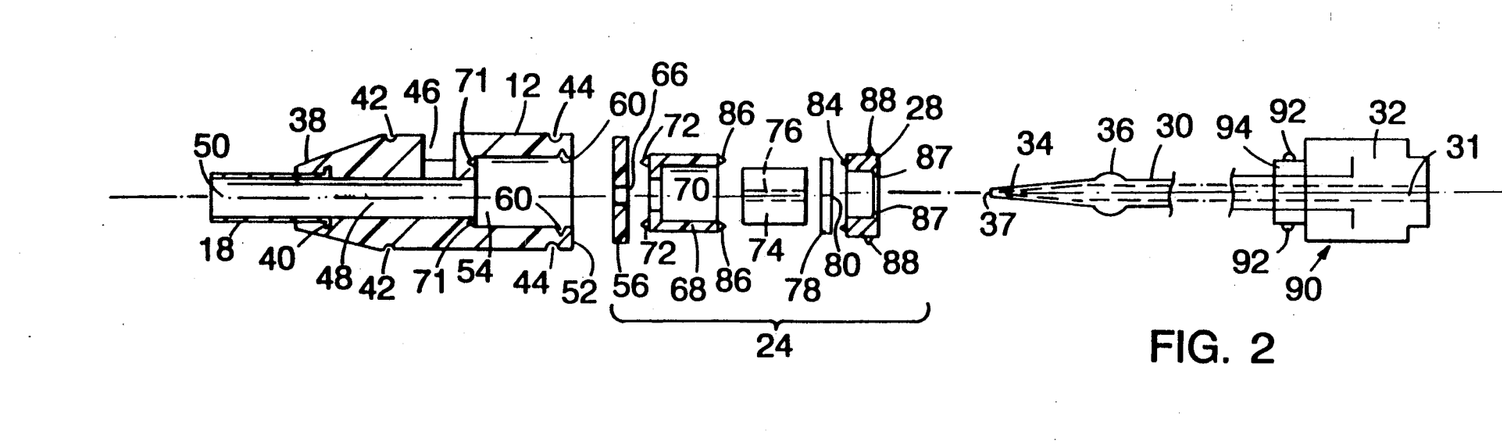
FIG. 2 is an exploded diagrammatic representation of components of a catheter introducer.

Referring to FIG. 2, introducer body 12 is formed of molded nylon, and has a tip 38 thermoformed around the proximal end of catheter 16, which is provided with a flange 40 to improve connection with the distal portion of introducer body 12. Introducer body 12 is provided with grooves 42, 44 suitable for connection with base 14, as described below. An aperture 46 extending through the body 12 provides for connection of tube 20 to central channel 48, and thence with the internal channel 50 of sheath 18. At the proximal end 52 of introducer body 12 there is formed a cup shaped orifice 54 for holding valve assembly 24, as discussed below. Groove 60 defined by the wall of orifice 54 is engaged by ridge 88 about cap 28 to hold valve assembly 24 in place.

Figure 3:
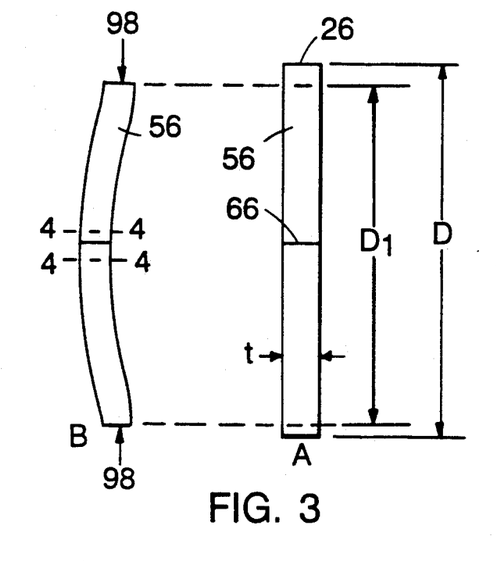
FIG. 3 is a transverse sectional view through a valve in its non-inserted state (A) and in its inserted state (B)

Valve assembly 24 consists of a valve element 56, valve cup 68, sponge 74, seal 78, and cap 28. Valve element 56 is formed, e.g., of silicone or natural latex, and has a central slit 66. Valve element 56 has a diameter about 10% greater than the inner diameter of orifice 54. Valve cup 68, e.g. of molded nylon, having a central aperture 70 and a circular ridge 72, is provided to push valve element 56 into place at the base of cup 54. Valve element 56 is held in this position by engagement of groove 71 defined by the wall of the orifice, and ridge 72, defined by valve cup 68. In this position, valve element 56 forms a dome shape (FIG. 3b). Within cup 68 is positioned sponge 74, e.g. of polyurethane, soaked with liquid silicone and having a central channel 76 of a diameter, e.g., slightly narrower than the outer diameter of dilator 30. An outer silicone or natural latex seal 78 is provided, having a central slit 80 of length 0.07 inch. The diameter of seal 78 is typically the same as the inner diameter of valve cup 54. Finally, cap 28, e.g. of molded nylon, is provided to hold the valve assembly 24 in place. Cap 28 has a circular ridge 84 which cooperates with a similar circular ridge 86 on valve cup 68 to hold seal 78 in position. Cap 28 also has a proximal ridge 87 for snap fit connection with ridge 92 of the hub of dilator assembly 90. Further, cap 28 has a circular ridge 88 for mating with groove 60 to tightly hold the hemostasis valve assembly 24 in place within cup 54.

Figure 4:
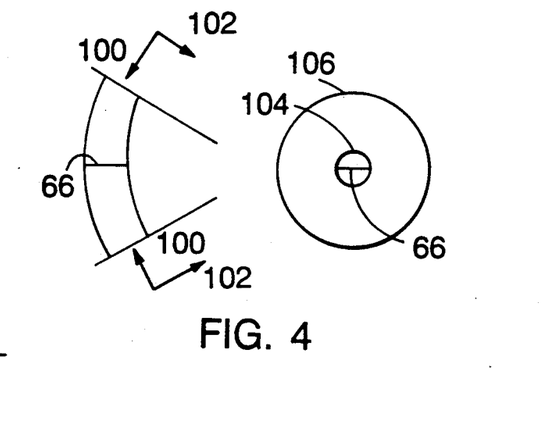
FIG. 4 is a force diagram taken from FIG. 3 at 4—4.

Referring to FIG. 3, valve element 56 has a diameter D (0.4375 inch) approximately 10% greater than $D_1$, the inner diameter of valve cup 54. Valve element 56 has a thickness, t, of about 0.04 inch. Slit 66 has a length of about 0.035 inch. In panel B, valve element 56 is shown in the dome shape, formed when the valve is positioned within valve cup 54 to form part of a valve assembly 24. This dome shape is formed by radial compression forces, shown generally by arrows 98. These forces are shown in detail in FIG. 4, where the major part of the forces acting on a free body element of valve element 56 are external radial compression forces 100 and shear forces 102.

Slit size 66 of valve element 56 is determined as the minimum size which allows the widest part of dilator 30, or other device to be employed with the introducer, to pass through it without forming a significant tear and without allowing leakage through valve element 56. This slit is not so large as to allow leakage when a guidewire, or other relatively smaller diameter tube, is passed through valve element 56. The size of slit 66 will depend upon diameters D and $D_1$, and upon thickness t of valve element 56. It will also depend upon the material used to form valve element 56. In the example given here and shown in FIG. 4, a slit 66 of 0.035 inch in length can be used to effectively seal a guidewire of diameter 0.035 inch (shown generally as 104) and a dilator or catheter (shown generally as 106) of diameter 0.105 inch. The slit is formed in a manner whereby essentially no material of the valve is removed.

Dilator assembly 90 (FIG. 2) is provided with a hub 32 having a distal connector 94 with circular ridge 92 which mates with ridge 87 when dilator 30 is pushed through valve assembly 24 and through introducer body 12. Also provided is the elongated dilator tube 30 having tapered proximal end 34 and ridge 36.

Figure 5:
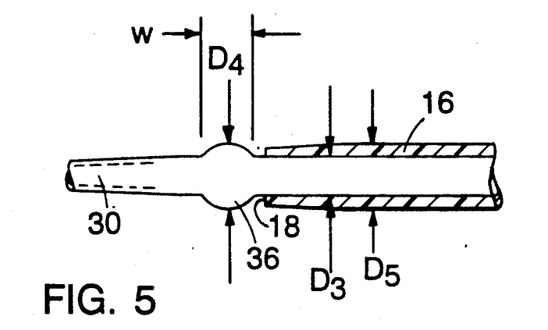
FIG. 5 is a partially longitudinal sectional view through a dilator and a catheter sheath.
Figure 6:
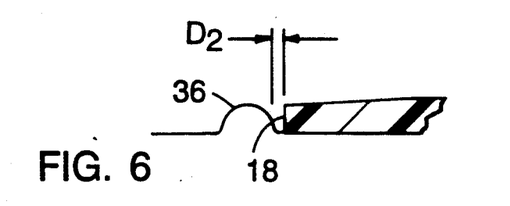
FIG. 6 is an expanded view of the junction between the catheter sheath and dilator.

Referring to FIG. 5, in its assembled form catheter introducer sheath 16 is disposed, by engagement of ridge 92 with ridge 87, with its distal end 18 disposed closely adjacent to ridge 36, such that when dilator 30 is inserted via a puncture opening into a body cavity over a guidewire, it prevents the body from seeing a blunt edge 18 and thus reduces the chance of trauma to the body and reduces the chance of damage to sheath 16 which might result in a sharp edge or corner that could damage the interior of the vessel into which the sheath is introduced. Preferably, as shown in FIG. 6, the distance between ridge 36 and the distal end 18 is a distance $D_2$ of up to 0.01 inch. Referring again to FIG. 5, for a dilator having a diameter $D_3$ of approximately 0.105 inch, ridge 36 has a diameter $D_4$ of approximately 0.112 inch and a width W of 0.056 inch. The sheath 16 has diameter $D_5$ of approximately 0.119 inch tapered to approximately 0.112 inch at the distal end 18, over a distance of 0.1 inch.

Figure 7:
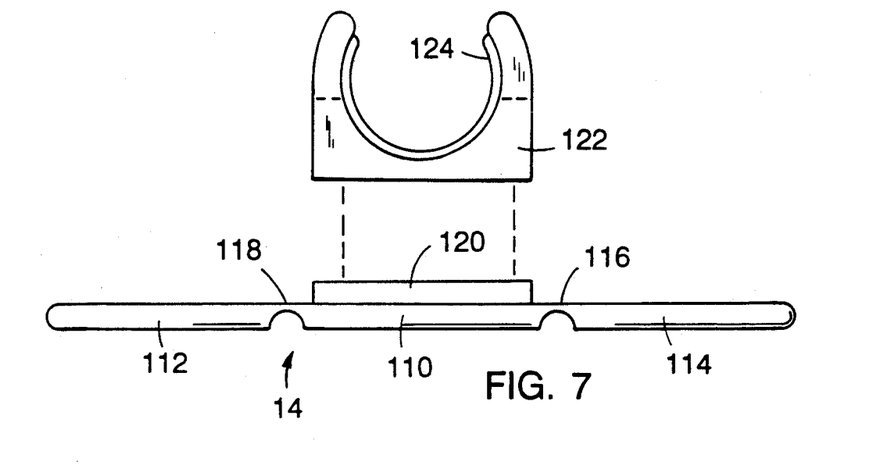
FIG. 7 is a transverse sectional view through a base.
Figure 8:
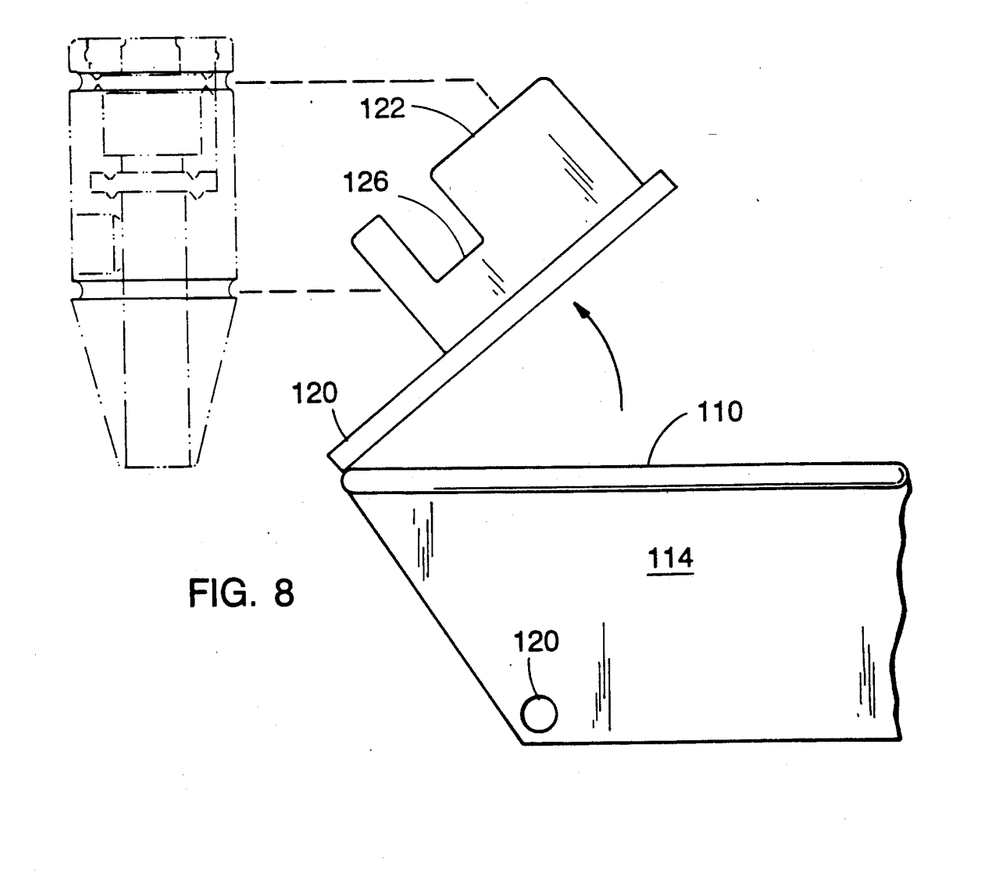
FIG. 8 is a partially isometric view of the base in longitudinal section, with the base in an inclined position.
Figure 9:
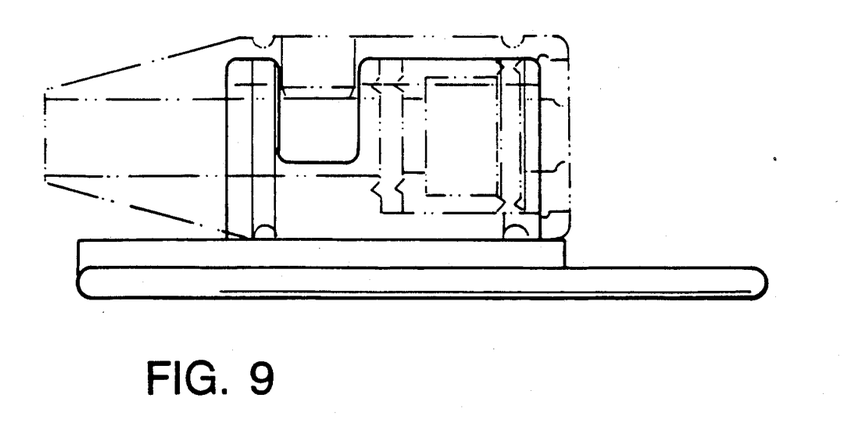
FIG. 9 is a partially isometric view of an introducer body attached to a base.

Referring to FIG. 7, base 14 has a generally flat central portion 110 and two wing portions 112, 114 connected by hinges 116, 118 to central portion 110. Also provided is a second central hinged portion 120 lying on top of flat portion 110. Connected to portion 120 is a connector 122 having two ridges 124 (only one is shown) suitable for connection with grooves 42, 44 on introducer body 12. As shown in FIG. 8, hinged portion 120 can be moved relative to portion 110. Connector 122 is provided with an aperture 126 which allows the introducer body 12 to be rotated to position tube 20 at the desired orientation.

Figure 10:
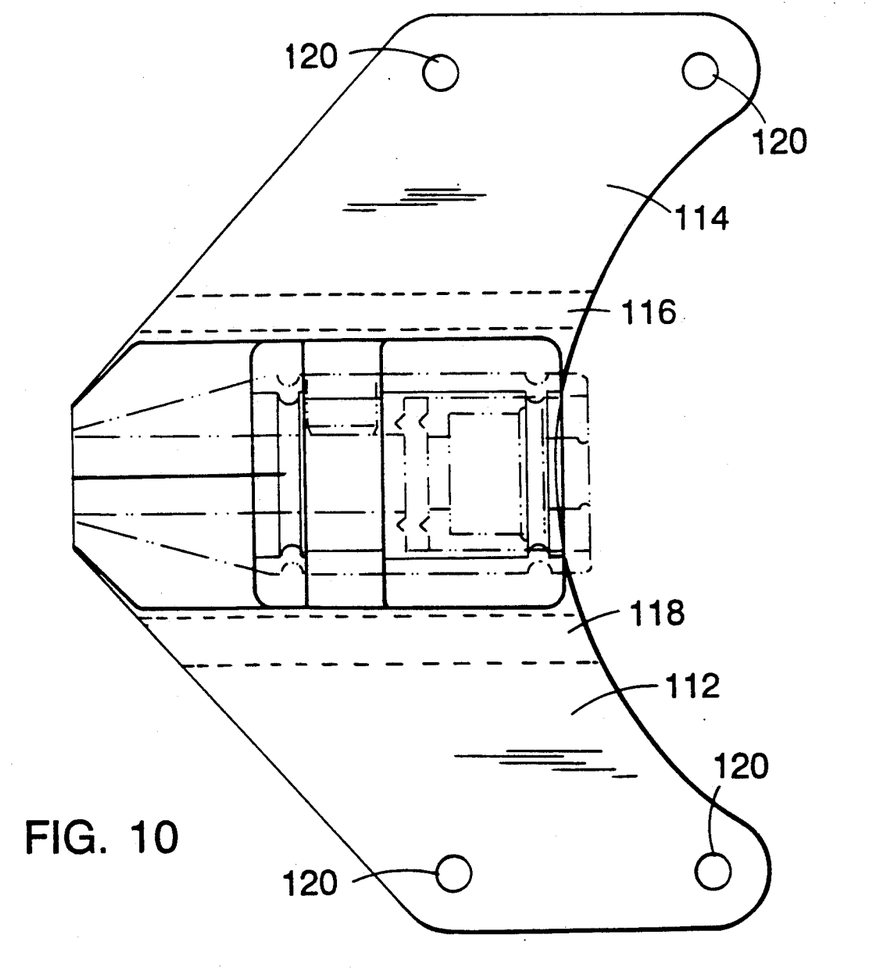
FIG. 10 is a top view of the introducer body and base in mated relationship.

Referring to FIG. 10, wing portions 112, 114 are provided with four apertures 120, suitable for temporarily suturing connector 122 to human tissue. Beneath these wings is also provided an adhesive layer (not shown) suitable for temporarily boning to human tissue to hold catheter introducer 10 in place.

ASSEMBLY

The components described above are manufactured by standard procedures. Valve assembly 24 is assembled by positioning valve element 56 over the proximal end of valve cup 54 and pushing it into orifice 54 using valve cup 68. Sponge 74 is then soaked in silicone and inserted into cup 68. Seal 78 is positioned over sponge 74 and valve cup 68 and cap 82 pushed over seal 78 such that ridge 88 is press fit into groove 60. Tube 20 is then glued into aperture 46. The assembled introducer body 12 is press fitted into connector 122 by mating ridges 124 with grooves 42, 44. Dilator 30 is then pushed through cap 82 to contact slit 80 of seal 78. Slit 80 opens to allow the distal end 34 of dilator 30 to enter aperture 76 of sponge 74. As dilator 30 passes through sponge 74, it is provided with a thin layer of silicone. Dilator 30 is then pushed through aperture 70 to slit 66. The siliconized distal tip 34 pushes slit 66 open to form an aperture through which the body of dilator 30 can be pushed. The whole length of dilator 30 is then pushed through slit 66 until ridge 92 is press fit past ridge 87. Dilator 30 is then held firmly in position. Referring to FIG. 5, in this position, distal portion 34 of dilator 30 is positioned distally from the distal end 18 of sheath 16. Further, ridge 36 is positioned a distance $D_2$ from distal end 18.

USE

Prior to use of catheter introducer 10 a needle is inserted into an appropriate body cavity, e.g., a blood vessel, and a guidewire inserted into the vessel through the center passage of the needle. The needle is then removed leaving the guidewire in place. The catheter introducer assembly is then inserted over the guidewire such that distal end 34 of dilator 30 enters the body cavity, followed by ridge 36, which is immediately followed by distal end 18 of sheath 16. The ridge 36 acts to expand the puncture opening gradually to ease passage of the blunt end of the sheath 16 therethrough with a lesser degree of trauma, and less chance of damage to the end of the sheath. The introducer is inserted to a desired depth, and dilator 30 removed by pulling o hub 32 to dissociate ridges 87, 92. The proximal surface of ridge 36 is also tapered to facilitate passage of the tip through the narrow end of the sheath. Blood, or other fluids, in the body cavity will enter channel 50 of sheath 18 and enter channel 48 of introducer body 12. However, valve element 56 prevents significant leakage of body fluids into valve assembly 24, since slit 66 closes as soon as dilator 30 is removed from it. Pressure from the body fluid against the convexly domed outer surface of the valve aids in closing slit 66. Any leakage into valve assembly 24 is prevented from leaving valve assembly 24 by seal 78 which also retards leakage of silicone from the sponge. If required, heparin or other chemicals may be directly administered through three-way valve 22 and tube 20 into aperture 48, distal of the valve assembly and thence aperture 50.

Other embodiments possible are within the scope of the following claims.

We claim:
1. A medical catheter introducer assembly including a hemostasis valve assembly comprising:
   an introducer sheath comprising an elongated tubular element defining an introducer conduit,
   an introducer housing disposed at the proximal end of said introducer sheath and further defining an introducer conduit therethrough and an orifice,
   a flexible elongated dilator sized and constructed for insertion through the conduit of said introducer housing and introducer sheath, said dilator having a tapered distal tip end portion and defining an axial dilator conduit therethrough, said dilator having an outer surface further defining an annular ridge having distally- and proximally-directed inclined surfaces,
   said introducer sheath, when assembled with said dilator, having its distal end immediately adjacent the proximally-directed inclined surface of the dilator ridge, and
   a hemostasis valve adapted for sealing said introducer conduit and disposed in alignment with said introducer conduit, said hemostasis valve having a wall surface defining a passageway for said dilator and said ridge therethrough wherein said wall surface defining said passageway is disposed in sealing engagement with the outer surface of said dilator, and adapted to seal when said dilator is removed,
   said hemostasis valve comprising a valve housing having a valve wall surface defining an orifice of a first, smaller diameter, and a disk-form valve element of a second diameter relatively greater than said first diameter, said valve element disposed within said orifice being subjected to externally-applied, radially directed forces as result of the valve element of said greater diameter bearing on the valve wall surface of said valve housing defining said orifice of said smaller diameter, causing predetermined compression of said valve element, said valve element adapted to assume a dome-shape formation under said predetermined compression, with a convex surface disposed against the pressure of fluids from a source within the body distal of said valve element, said pressure being on the order of a few psi, wherein said disk-form valve element has a preselected thickness and diameter to allow said pressure of said body fluid against said convex domed outer surface to enhance the seal between the wall surface of said passageway and the outer surface of the dilator,
   whereby, as said introducer assembly is introduced into a body over a guidewire extending via a puncture opening into a body vessel, said dilator and sheath are adapted to flex to follow said guidewire, and the tapered end portion of said dilator and the distally-directed inclined surface of said dilator ridge act to dilate the flesh about said opening to facilitate passage of said sheath therethrough.
2. The introducer assembly of claim 1 wherein said ridge is immediately distal of the tapered portion of said dilator.
3. The introducer assembly of claim 1 wherein said dilator further comprises a proximal hub, and said introducer housing and said dilator hub define cooperating means for fixedly positioning the distal end of the introducer sheath immediately adjacent the proximally-directed inclined surface of said dilator ridge.

4. The introducer assembly of claim 1 wherein said introducer housing defines a second conduit for passage of fluid into the conduit defined by said introducer sheath.

5. The introducer assembly of claim 4 wherein said second conduit is distal of said hemostasis valve.

6. A hemostasis valve assembly adapted for sealing a conduit connected to a vessel of the body, said valve having a wall surface defining a passageway for catheter or the like therethrough with said valve disposed thereabout wherein said wall surface defining said passageway is disposed in sealing relationship with the outer surface of said catheter or the like, and said valve adapted to seal said conduit with said catheter removed, said hemostasis valve comprising:

a valve housing having a valve wall surface defining an orifice of a first, smaller diameter, and a disk-form valve element of a second diameter relative greater than said first diameter, said valve element disposed within said orifice being subjected to externally-applied, radially directed forces as result of the valve element of said greater diameter bearing on the portion of valve wall surface of said valve housing defining said orifice of said smaller diameter to cause predetermined compression of said valve element, said valve element adapted to assume a dome-shape formation under said predetermined compression, with a convex surface disposed against the pressure of fluids from a source within the body distal of said valve element, said pressure being on the order of a few psi, where said disk-form valve element has a preselected thickness and diameter to allow said pressure of said body fluid against said convex domed outer surface to enhance the seal between the wall surface of said passageway and the outer surface of the catheter and the like.

7. The assembly of claim 1 or 6 wherein said second diameter is about 10% greater than said first diameter.

8. The assembly of claim 1 wherein said hemostasis valve assembly further comprises a valve cup element defining an orifice and, disposed therewithin, lubricating means for lubricating a catheter or the like for encounter with the passageway of the valve, and a seal means for retaining lubricant within said introducer housing.

9. The assembly of claim 8 wherein said lubricating means comprises a silicone soaked sponge.

10. The assembly of claim 8 wherein said introducer housing and said valve cup define cooperating means for engaging opposite surfaces of said valve element for holding the valve element in position within said introducer housing.

11. The assembly of claim 6 wherein said hemostasis valve assembly further comprises a valve cup element defining an orifice and, disposed therewithin, lubricating means or lubricating a catheter or the like for encounter with the aperture of the valve element, and a seal means for retaining lubricant within said valve housing.

12. The assembly of claim 11 wherein said lubricating means comprises a silicone soaked sponge.

13. The assembly of claim 11 wherein said valve housing and said valve cup define cooperating means or engaging opposite surfaces of said valve element for holding the valve element in position within said valve housing.

* * * * *

UNITED STATES PATENT AND TRADEMARK OFFICE
CERTIFICATE OF CORRECTION

PATENT NO. : 5,098,393
DATED : March 24, 1992
INVENTOR(S) : Amplatz et al.

It is certified that error appears in the above-identified patent and that said Letters Patent is hereby corrected as shown below:

Col. 5, line 7; "boning" should be --bonding-- line 50; "o" should be --on--

Col. 8, line 15, after "claim 8" insert --or 9--

Signed and Sealed this

Twenty-fourth Day of August, 1993

Attest:

BRUCE LEHMAN

Attesting Officer    Commissioner of Patents and Trademarks